(12) United States Patent
Valbuena et al.

(10) Patent No.: US 10,413,325 B2
(45) Date of Patent: Sep. 17, 2019

(54) SYSTEMS AND METHODS FOR IMPLANTING AN IMPLANTABLE CARDIAC MONITOR

(71) Applicant: PACESETTER, INC., Sylmar, CA (US)

(72) Inventors: Abigail Valbuena, Santa Clara, CA (US); Gene A. Bornzin, Simi Valley, CA (US); Zoltan Somogyi, Simi Valley, CA (US); Didier Theret, Porter Ranch, CA (US)

(73) Assignee: PACESETTER, INC., Sylmar, CA (US)

( * ) Notice: Subject to any disclaimer, the term of this patent is extended or adjusted under 35 U.S.C. 154(b) by 4 days.

(21) Appl. No.: 15/438,535

(22) Filed: Feb. 21, 2017

(65) Prior Publication Data

US 2017/0156754 A1    Jun. 8, 2017

Related U.S. Application Data

(62) Division of application No. 14/576,004, filed on Dec. 18, 2014, now abandoned.

(51) Int. Cl.
*A61B 17/34* (2006.01)
*A61B 5/02* (2006.01)
*A61B 5/00* (2006.01)
*A61M 37/00* (2006.01)

(52) U.S. Cl.
CPC ............ *A61B 17/3468* (2013.01); *A61B 5/02* (2013.01); *A61B 5/6861* (2013.01); *A61B 17/3417* (2013.01); *A61B 5/686* (2013.01); *A61B 2017/3454* (2013.01); *A61B 2017/3456* (2013.01); *A61B 2560/063* (2013.01); *A61M 37/0069* (2013.01)

(58) Field of Classification Search
CPC .................................................... A61B 5/686
See application file for complete search history.

(56) References Cited

U.S. PATENT DOCUMENTS

| 5,405,324 | A  | * | 4/1995  | Wiegerinck | ....... A61M 37/0069 600/567 |
| 9,572,970 | B2 | * | 2/2017  | Vanderpool | ....... A61M 37/0069 |
| 2010/0331868 | A1 | * | 12/2010 | Bardy | ............... A61M 37/0069 606/167 |

* cited by examiner

*Primary Examiner* — Joseph M Dietrich

(57) ABSTRACT

The present disclosure provides systems and methods for implanting an implantable cardiac monitor. An injection system includes an implantable cardiac monitor (ICM), a plunger, a plunger handle coupled the plunger, and an injector housing. The injector housing includes a tube extending from a first end of the injector housing to a second end of the injector housing, the tube configured to receive the ICM and the plunger, and at least one leaflet formed at the second end of the injector housing, the at least one leaflet configured to rotate outward when a user operates the plunger handle to push the ICM through the injector housing second end via the plunger.

14 Claims, 6 Drawing Sheets

SYSTEMS AND METHODS FOR IMPLANTING AN IMPLANTABLE CARDIAC MONITOR

CROSS REFERENCE TO RELATED APPLICATIONS

This application is a division of U.S. patent application Ser. No. 14/576,004, filed Dec. 18, 2014.

FIELD OF THE DISCLOSURE

The present disclosure relates generally to implantable cardiac monitors (ICMs), and more par to systems and methods for implanting ICMs.

BACKGROUND ART

Implantable cardiac monitors (ICMs) are devices that may be implanted under a patient's skin to continuously monitor the patients cardiac activity. An ICM may be programmed to detect and record cardiac information and episodes such as atrial/ventricular tachycardia, atrial fibrillation, bradycardia, asystole, etc. Triggers for detecting and recording an event (e.g., such a tachy/brady detection rate, a number of events, and/or a duration of asystole) may be programmed by a clinician. Alternatively, when the patient experiences symptoms, the patient may activate the detection and recording using an external patient activator. Diagnostics and recorded events may be downloaded by the clinician in-clinic using a programmer. Further, the data may also be transmitted to the clinician using a daily remote monitoring system.

As compared to external cardiac monitors, ICMs allow clinicians to monitor the patient's cardiac activity for an extended period of time, with an average longevity of up to 36 months. The information recorded by ICMs enables clinicians to determine if a patient complaining of symptoms has irregularities in their heart rhythm that cannot be confirmed in the clinic. The information can also aid the clinician in determining the best course of treatment for the patient (e.g., an addition or change of medication, a procedure such as cardioversion or ablation to restore a regular heart rhythm, and/or implantation of a pacemaker or implantable cardioverter defibrillator for long-term treatment of an irregular heart rhythm).

ICMs are generally relatively small (e.g., 1.1-1.5 cm$^3$ in volume), and can be implanted using a relatively small incision (e.g., 1 cm). Once inserted under the patient's skin, the ICM has a relatively slim profile, mitigating patient concerns about body image. The ICM may be implanted in the patient's chest area near the sternum, and the implant procedure may take less than 10 minutes after application of a local topical anesthesia. Further, ICMs do not deliver pacing or shock therapies to the patient, nor do they require leads to be implanted in the patient's heart.

At least one known method for implanting ICMs includes creating an incision, inserting a tool into the incision and rotating it to create a pocket under this skin, and inserting the ICM using a plunger system that pushes the device in and uses the tool as a guide. However, using at least some known insertion systems, the incision may be relatively difficult to keep open during the procedure. Further, it may be relatively difficult to maneuver the tool into the tissue to position the ICM. For patients with taut tissue, additional force may be required to insert the ICM, while for patients with loose tissue, the ICM may move after implant if a pocket created for the ICM is relatively large. Moreover, in at least some known insertion systems, it may be relatively difficult to push the ICM, which typically has rounded edges, into tissue. Finally, once the ICM is implanted, at least some known insertion systems are relatively difficult to remove from the patient.

BRIEF SUMMARY OF THE DISCLOSURE

In one embodiment, the present disclosure is directed to an injection system. The injection system includes an implantable cardiac monitor (ICM), a plunger, a plunger handle coupled the plunger, and an injector housing. The injector housing includes a tube extending from a first end of the injector housing to a second end of the injector housing, the tube configured to receive the ICM and the plunger, and at least one leaflet formed at the second end of the injector housing, the at least one leaflet configured to rotate outward when a user operates the plunger handle to push the ICM through the injector housing second end via the plunger.

In another embodiment, the present disclosure is directed to a method for operating an injection system. The method includes inserting an implantable cardiac monitor (ICM) into a tube of an injector housing, wherein the tube extends from a first end of the injector housing to a second end of the injector housing, and wherein the second end of the injector housing includes at least one leaflet configured to rotate outward when the ICM is pushed through the injector housing second end. The method further includes inserting a plunger into the tube, wherein the plunger is coupled to a plunger handle.

In another embodiment, the present disclosure is directed to an injection system. The injection system includes an implantable cardiac monitor (ICM), and an obturator including a tip, a handle, and a shaft extending between the tip and the handle. The injection system further includes an injector housing including a tube extending from a first end of the injector housing to a second end of the injector housing, the tube configured to receive the obturator, and a receptacle in communication with the tube and an external environment, the receptacle configured to receive the ICM.

In another embodiment, the present disclosure is directed to a method for operating an injection system. The method includes inserting an obturator into a tube of an injector housing such that the obturator extends from a first end of the injector housing to a second end of the injector housing, and inserting an implantable cardiac monitor (ICM) into a receptacle of the injector housing, wherein the receptacle is in communication with the tube of the injector housing.

The foregoing and other aspects, features, details, utilities and advantages of the present disclosure will be apparent from reading the following description and claims, and from reviewing the accompanying drawings.

BRIEF DESCRIPTION OF THE DRAWINGS

Corresponding reference characters indicate corresponding parts throughout the several views of the drawings.

DETAILED DESCRIPTION OF THE DISCLOSURE

The present disclosure provides systems and methods for implanting an implantable cardiac monitor. An injection system includes an implantable cardiac monitor (ICM), a plunger, a plunger handle coupled the plunger, and an injector housing. The injector housing includes a tube extending from a first end of the injector housing to a second end of the injector housing, the tube configured to receive the ICM and the plunger, and at least one leaflet formed at the second end of the injector housing, the at least one leaflet configured to rotate outward when a user operates the plunger handle to push the ICM through the injector housing second end via the plunger.

Figure 1:
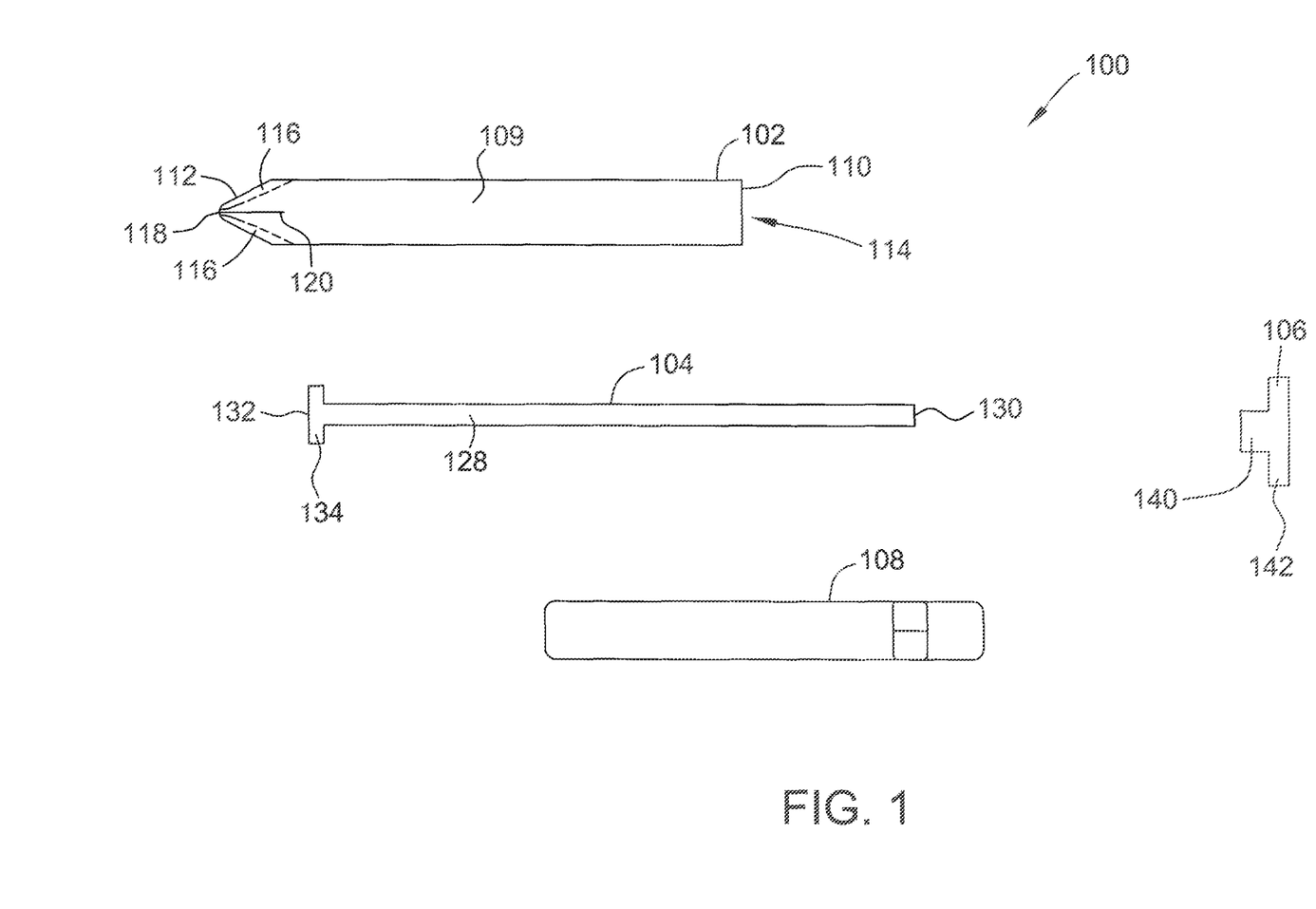
FIG. 1 is a schematic view of one embodiment of an implantable cardiac monitor (ICM) injection system.
Figure 2A:
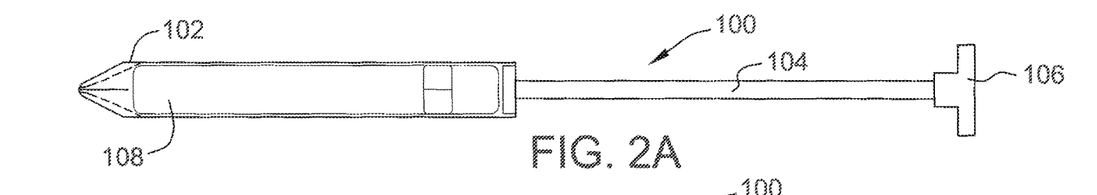
FIGS. 2A-2E are schematic views illustrating operation of the injection system of FIG. 1.

Referring now to the drawings and in particular to FIG. 1, an implantable cardiac monitor (ICM) injection system is indicated generally at 100. Components of injection system 100 include an injector housing 102, a plunger 104, a plunger handle 106, and an ICM 108. In FIG. 1, the components of injection system 100 are shown separate from one another (i.e., in a disassembled state). In FIG. 2A, the components of injection system 100 are shown in an assembled state.

Injector housing 102 includes a tube 109 that extends from a first end 110 to a second end 112. In this embodiment, tube 109 is substantially cylindrical. Alternatively, tube 109 may have any shape that enables injection system 100 to function as described herein. For example, in some embodiments, tube 109 may have substantially arcuate inner and/or outer surfaces on sides of tube 109 and substantially flat inner and/or outer surfaces on a top and a bottom of tube 109.

In this embodiment, tube 109 has an inner diameter that is slightly larger than a diameter of ICM 108, such that ICM 108 is positionable within tube 109. First end 110 includes an opening 114 to facilitate inserting ICM 108 and plunger 104 into injector housing 102. Second end 112 includes a plurality of triangular leaflets 116 that taper to a point 118. Leaflets 116 are formed by slits 120 extending from point 118. In the illustrated embodiment, second end 112 includes four slits 120 that form four leaflets 116. Alternatively, second end 112 may include any number and/or configuration of slits 120 and leaflets 116 that enable injector housing 102 to function as described herein. Leaflets 116 facilitate propping open an opening formed by an incision, as described herein.

To implant ICM 108, injector housing 102 is inserted into an incision. Accordingly, injector housing 102 should be relatively firm to maintain its shape as injector housing 102 is inserted into the incision. Accordingly, injector housing may be fabricated from, for example, polycarbonate. In some embodiments, leaflets 116 are fabricated from a firmer material (e.g., stainless steel) to facilitate propping open the incision.

In the illustrated embodiment, plunger 104 includes a substantially cylindrical shaft 128 that extends from a first end 130 to a second end 132. Alternatively, shaft 128 may have any shape that enables plunger 104 to function as described herein. Plunger handle 106 couples to first end 130 using, for example, a snap-fit engagement. Second end 132 includes an annular flange 134 that has a larger diameter than shaft 128, but a smaller diameter than the inner diameter of tube 109. Accordingly, annular flange 134 is insertable within tube 109. Plunger 104 may be fabricated from, for example, polycarbonate.

As shown in FIG. 1, plunger handle 106 includes a first annular portion 140 and a second annular portion 142. First annular portion 140 has a diameter smaller than the inner diameter of tube 109, and second annular portion 142 has a diameter larger than the inner diameter of tube 109. Accordingly, when advancing plunger 104 through injector housing 102, first annular portion 140 is insertable into tube 109, but injector housing 102 contacts second annular portion 142 and prevents second annular portion 142 from being inserted into tube 109. Plunger handle 106 may be fabricated from, for example, polycarbonate or silicone.

To assemble injection system 100, as shown in FIG. 2A, ICM 108 is inserted into injector housing 102, and a portion of plunger 104 (i.e., annular flange 134) is inserted into injector housing 102. Injection system 100 may be packaged and distributed to clinicians in a fully assembled (i.e., pre-loaded) configuration. Alternatively, the components of injection system 100 may be assembled on-site where the implantation procedure is to take place.

A method of implanting ICM 108 using injection system 100 will now be described with respect to FIGS. 2A-2E. An incision (e.g., a 6 millimeter (mm) incision) is made in the patient using, for example, a surgical scalpel. Injector housing second end 112 is inserted through the incision into the patient's tissue. The tapered shape of second end 112 provides a relatively small spear-shaped entry point into the tissue. To push injection system 100 (and consequently ICM 108) further into the tissue, the clinician may rotate, torque, and maneuver injector housing 102.

To implant ICM 108, using plunger handle 106, the clinician pushes plunger 104 further into injector housing 102 such that plunger 104 moves relative to injector housing 102. As shown in FIGS. 2B-2E, pushing plunger 104 in turn pushes ICM 108 through injector housing 102. When ICM 108 reaches second end 112, ICM 108 contacts leaflets 116 and pushes and rotates leaflets 116 outward. When leaflets 116 spread outward, they keep the incision opening propped open while ICM 108 continues to be deployed.

Figures 2B, 2C, 2D, 2E:
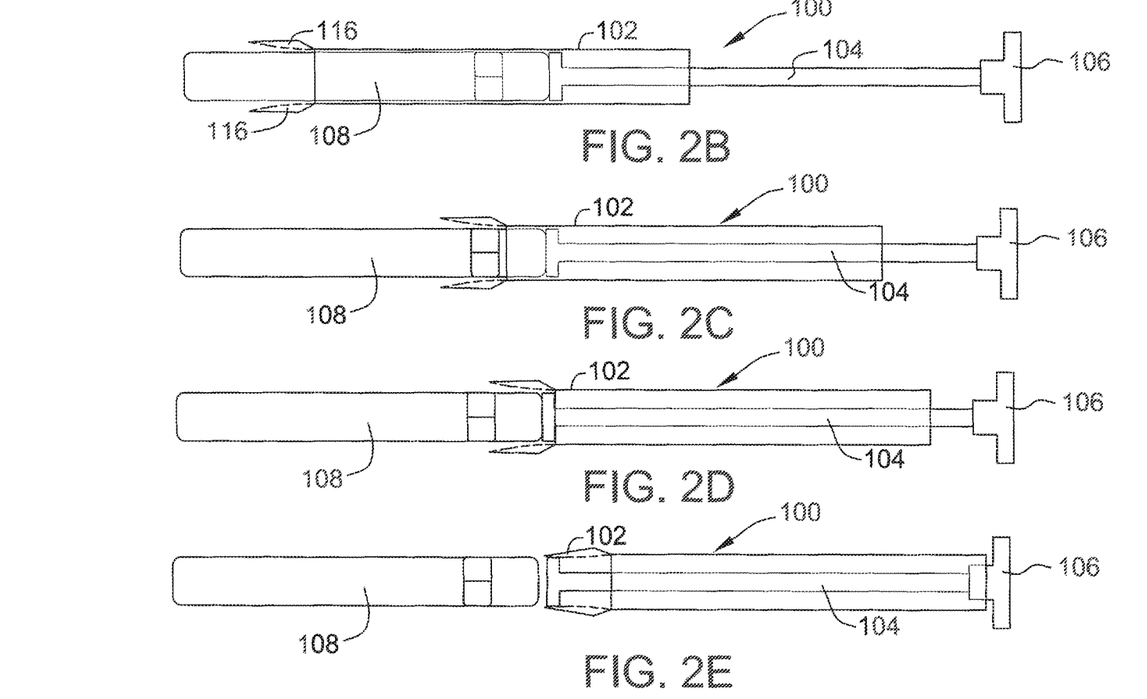

The clinician continues to push plunger 104 until second annular portion 142 of plunger handle 106 contacts injector housing first end 110. In the illustrated embodiment, the length of plunger 104 is approximately equal to the length of injector housing 102. Accordingly, as shown in FIG. 2E, when plunger handle 106 contacts injector housing first end 110, ICM 108 is fully deployed (i.e., ICM 108 is positioned entirely outside of injector housing 102). This enables the clinician to confirm that ICM 108 is fully deployed in the tissue, even though the clinician will generally be unable to visually confirm the position of ICM 108. After ICM 108 is deployed, the clinician removes injector housing 102 (e.g., by pulling plunger handle 106) from the incision and closes the incision using known techniques (e.g., adhesive strips, sutures, etc.).

Figure 3A:
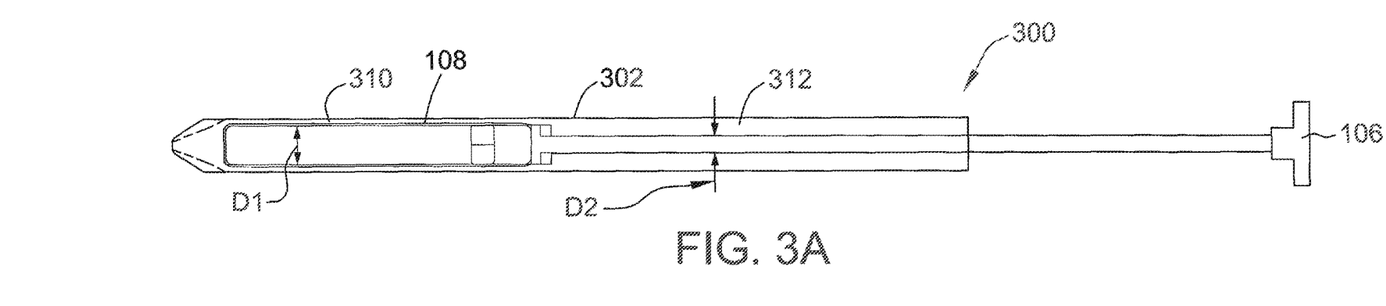
FIGS. 3A-3C are schematic views illustrating operation of one embodiment of an alternative injection system.
Figures 3B, 3C:
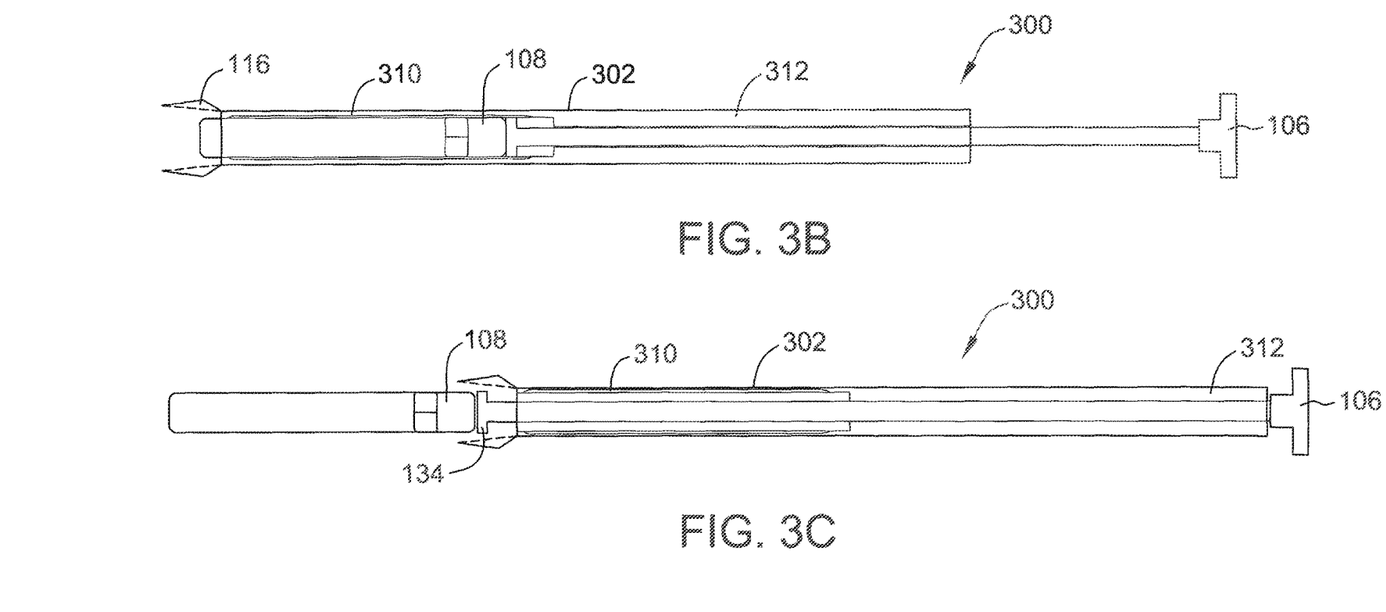

FIGS. 3A-3C are schematic diagrams of an alternative injection system 300. Unless otherwise indicated, injection system 300 operates substantially similar to injection system 100. As compared to injector housing 102, an injector housing 302 of injection system 300 includes a first tube portion 310 and a second tube portion 312. As shown in FIGS. 3A-3C, first tube portion 310 has a first inner diameter, D1, that is larger than a second inner diameter, D2, of second tube portion 312. Specifically, inner diameter D1 is slightly larger than the diameter of ICM 108 and the diameter of annular flange 134 of plunger 104. However, inner diameter D2 is smaller than the diameter of ICM 108 and the diameter of annular flange 134, but larger than the diameter of shaft 128 of plunger 104. Further, in the illustrated embodiment, inner diameter D2 is smaller than a diameter of first annular portion 140 of plunger handle 106.

When implanting ICM 108 using injection system 300, the clinician pushes plunger 104 until first annular portion 140 of plunger handle 106 contacts second tube portion 312 of injector housing 302. In the illustrated embodiment, the length of plunger 104 is approximately equal to the length of injector housing 302. Accordingly, as shown in FIG. 3C, when plunger handle 106 contacts second tube portion 312, ICM 108 is fully deployed (i.e., ICM 108 is positioned entirely outside of injector housing 302). Similar to injection system 100, this enables the clinician to confirm that ICM 108 is fully deployed in the tissue, even though the clinician will generally be unable to visually confirm the position of ICM 108. After ICM 108 is deployed, the clinician removes injector housing 302 (e.g., by pulling plunger handle 106) from the incision and closes the incision using known techniques (e.g., adhesive strips, sutures, etc.).

In injection system 300, in the illustrated embodiment, injector housing 302 and plunger 104 are both longer than in injection system 100. The longer overall length of injection system 300 may provide more control to the clinician during the implantation procedure.

Figure 4:
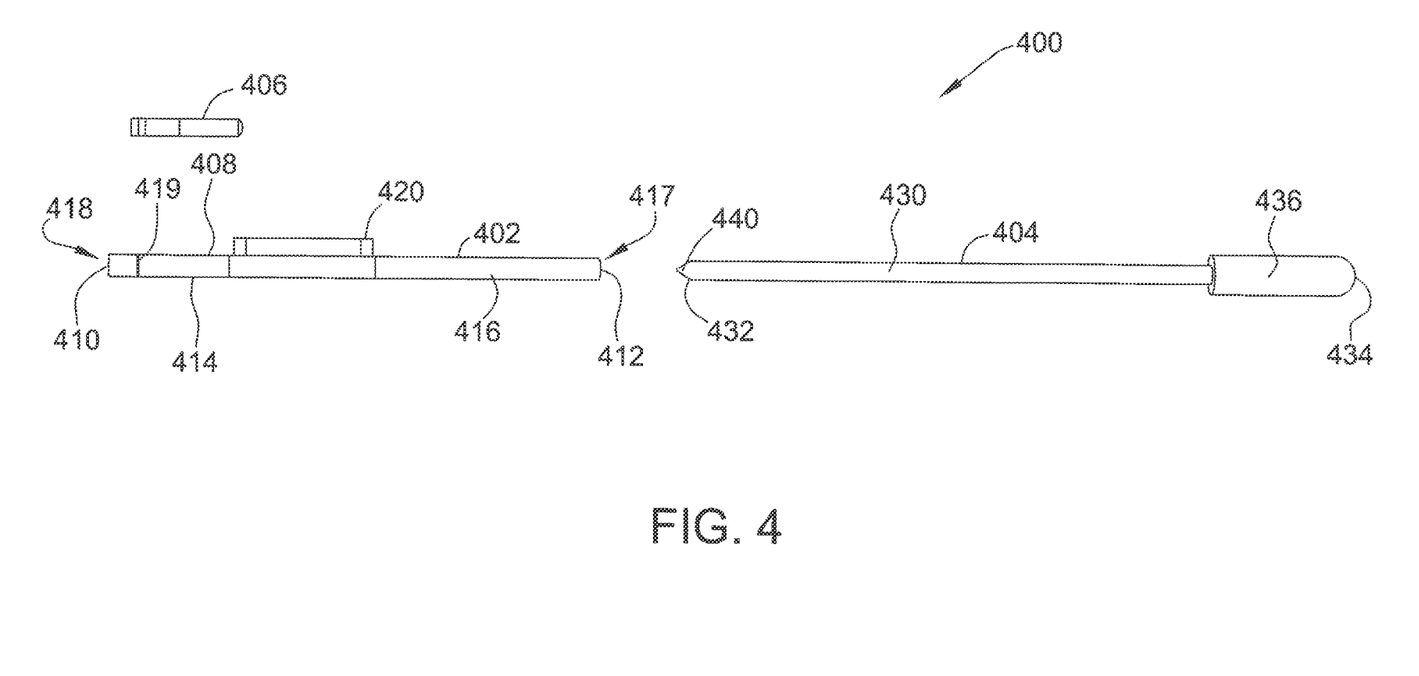
FIG. 4 is a schematic view of one embodiment of an alternative injection system.

FIG. 4 is a schematic diagram of an alternative ICM injection system 400. Components of injection system 400 include an injector housing 402, an obturator 404, and an ICM 406. In FIG. 4, the components of injection system 400 are shown separate from one another (i.e., in a disassembled state). In FIG. 5B (described in detail below), the components of injection system 400 are shown in an assembled state.

Injector housing 402 includes a substantially cylindrical tube 408 that extends from a first end 410 to a second end 412. Tube 408 includes a first tube portion 414 proximate first end 410 and a second tube portion 416 proximate second end 412. In the illustrated embodiment, first tube portion 414 has an inner diameter that is slightly smaller than an inner diameter of second tube portion 416. Alternatively, first and second tube portions 414 and 416 may have substantially the same inner diameter. Both first and second tube portions 414 and 416 have inner diameters that are larger than a diameter of ICM 406, such that ICM 406 is positionable within tube 408, as described in detail herein. Second end 412 includes an opening 417 to facilitate inserting obturator 404 into injector housing 402. Injector housing 402 includes another opening 418 at first end 410 to facilitate discharging ICM 406 from injector housing 402 into the patient.

Injector housing 402 includes an indicator 419 proximate first end 410. Indicator 419 facilitates aligning injector housing 402 during an implantation procedure, as described herein. In the illustrated embodiment, indicator 419 is a colored (e.g., red) band formed on the outside of first tube portion 414. Alternatively, indicator 419 may be any indicia and/or feature that enables indicator 419 to function as described herein. In some embodiment, injection systems 100 and 300 include a similar indicator. Injector housing 402 may be fabricated from, for example, polycarbonate, polysulfone, or another similarly resilient material.

Injector housing 402 further includes a receptacle 420 in communication with second tube portion 416 and in communication with an external environment 423. FIG. 6 is a perspective view of receptacle and ICM 406. As shown in FIG. 6, Receptacle 420 is sized to receive ICM 406. In the illustrated embodiment, receptacle 420 includes two opposing projections 422. Once ICM 406 is inserted into receptacle 420, projections 422 facilitate preventing ICM 406 from falling out of receptacle 420 into ambient environment 423. For example, projections 422 may engage ICM 406 in a snap-fit engagement to facilitate maintaining ICM 406 in receptacle 420. As shown in FIG. 5B, when ICM 406 is inserted into receptacle 420, obturator 404 is already inserted into first and second tube portions 414 and 416. Accordingly, obturator 404 initially prevents ICM 406 from entering second tube portion 416.

Obturator 404 includes a substantially cylindrical shaft 430 that extends from a first end 432 to proximate a second end 434. A rounded obturator handle 436 is formed at second end 434 of obturator 404. In the illustrated embodiment, obturator handle 436 is integrally formed with cylindrical shaft 430. Alternatively, obturator handle 436 may be releasably coupled to cylindrical shaft 430. Obturator handle 436 has a diameter that is larger than the diameter of cylindrical shaft 430 and the inner diameter of second tube portion 416.

A tip 440 is formed at first end 432 of obturator 404. Tip 440 is configured to perform blunt dissection in subcutaneous tissue of the patient. In the illustrated embodiment, tip 440 has a tapered conical shape. Alternatively, tip 440 may have any shape that enables obturator 404 to function as described herein. For example, tip 440 may have an oval shape, a duckbill shape, a wedge shape, a hook shape, and/or any other suitable shape. Obturator 404 may be fabricated from, for example, polycarbonate, polysulfone, or another similarly resilient material. In some embodiments, for comfort and/or usability, obturator handle 436 is formed from a softer material (e.g., silicone).

Figure 5A:
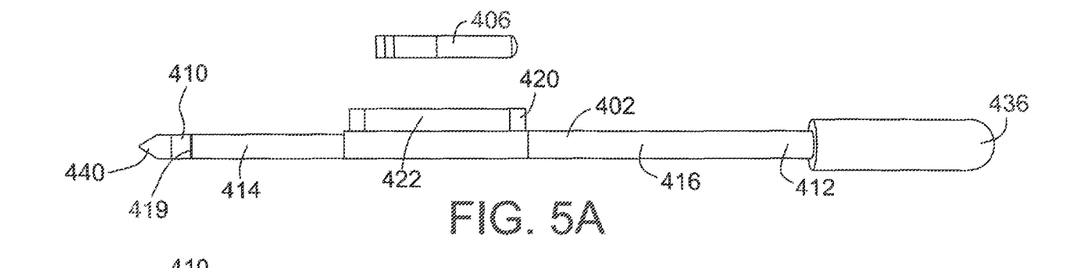
FIGS. 5A-5D are schematic views illustrating operation of the injection system of FIG. 4.
Figures 5B, 5C, 5D:
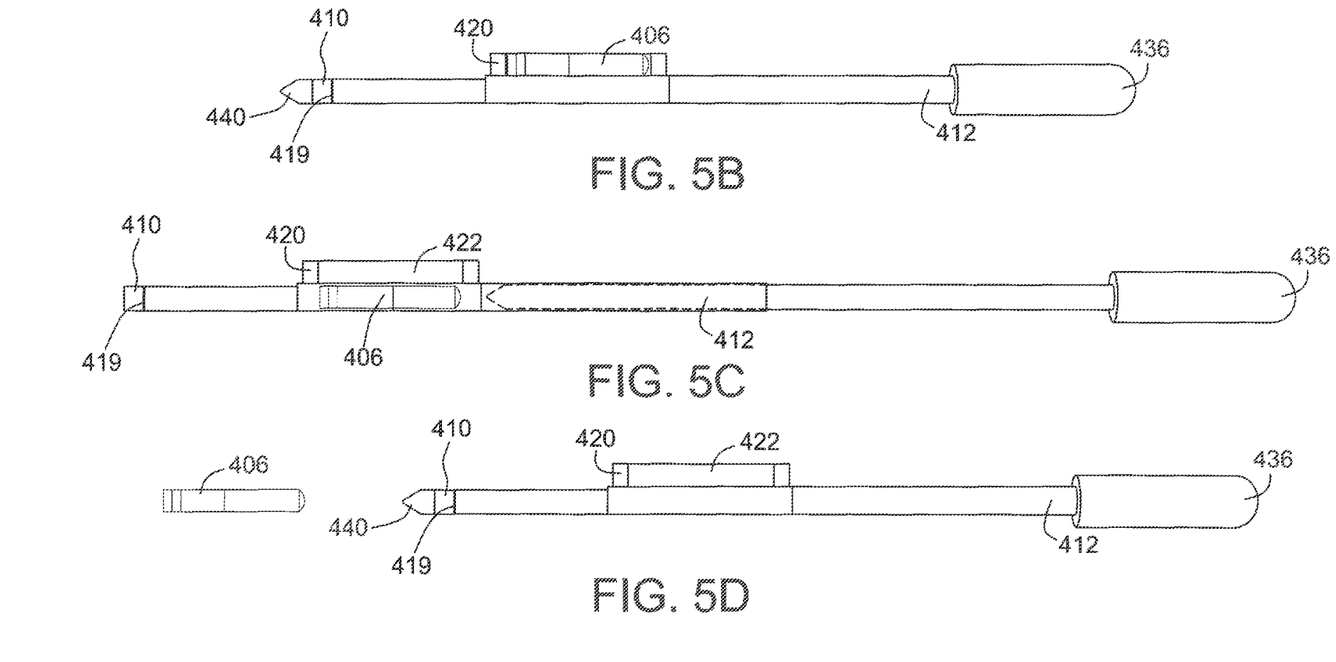
Figure 6:
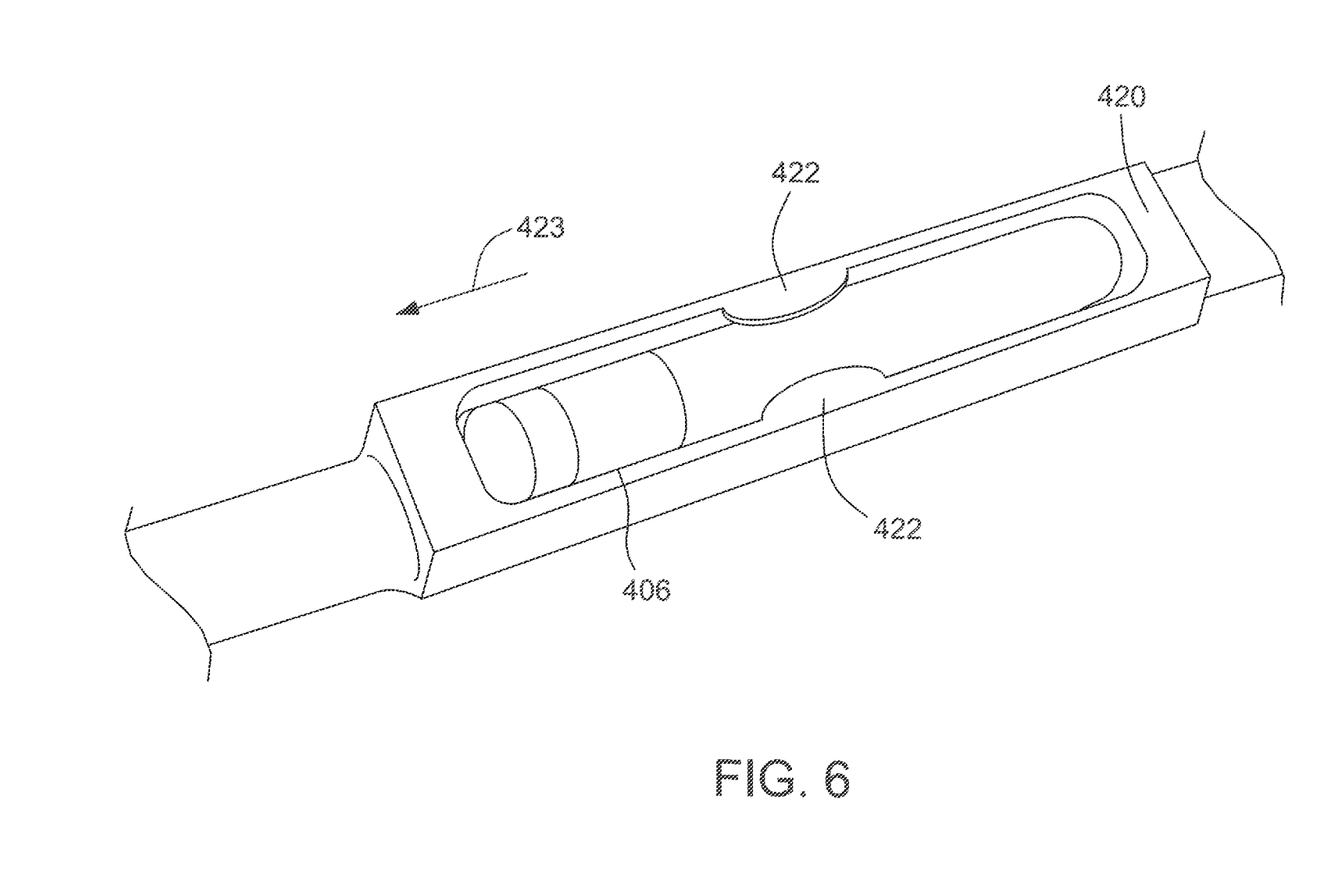
FIG. 6 is a perspective view of a portion of the injection system of FIG. 4.

To assemble injection system 400, as shown in FIGS. 5A and 5B, obturator 404 is inserted into first and second tube portions 414 and 416, and ICM 406 is inserted into receptacle 420. Injection system 400 may be packaged and distributed to clinicians in a fully assembled (i.e., pre-loaded) configuration. Alternatively, the components of injection system 400 may be assembled on-site where the implantation procedure is to take place.

A method of implanting ICM 406 using injection system 400 will now be described with respect to FIGS. 5A-5D. An incision (e.g., a 6 millimeter (mm) incision) is made in the patient using, for example, a surgical scalpel. With obturator 404 inserted into injector housing 402 and ICM 406 inserted into receptacle 420, injector housing first end 410 is inserted through the incision into the patient's tissue. As shown in FIG. 5B, tip 440 extends beyond first end 410 and provides a relatively small spear-shaped entry point into the tissue. At this point, tip 440 is used to perform blunt dissection in subcutaneous tissue of the patient, in preparation for the deployment of ICM 406. To form a cylindrical channel for ICM 406 below the patient's skin, the injector housing may be advanced until receptacle 420 reaches the incision.

Once blunt dissection is completed, obturator 404 is pulled back partially out of injector housing 402 in a first direction (i.e., towards injector housing second end 412), as shown in FIG. 5B. Once tip 440 passes ICM 406 and receptacle 420, ICM 406 drops (i.e., due to gravity) from receptacle 420 into second tube portion 416, and in front of obturator 404.

To position injector housing 402 for deployment of ICM 406, injector housing 402 is pulled out of the patients tissue until indicator 419 is visible. This enables the clinician to confirm that a relatively small portion of first tube portion 414 remains in the tissue, and that opening 418 is proximate a deployment site for ICM 406.

To deploy ICM 406, obturator 404 is advanced into injector housing 402 in a second direction opposite the first direction, pushing ICM 406 through first tube portion 414 and eventually out of opening 418. The clinician continues to push obturator 404 until obturator handle 436 contacts injector housing second end 412. In the illustrated embodiment, the length of obturator 404 is approximately equal to the length of injector housing 402. Accordingly, as shown in FIG. 6D, when obturator 404 contacts injector housing second end 412, ICM 406 is fully deployed (i.e., ICM 406 is positioned entirely outside of injector housing 402). This enables the clinician to confirm that ICM 406 is fully deployed in the tissue, even though the clinician will generally be unable to visually confirm the position of ICM 406. After ICM 406 is deployed, the clinician removes injector housing 402 from the incision (e.g., by pulling obturator handle 436) and closes the incision using known techniques (e.g., adhesive strips, sutures, etc.).

The ICM injection systems and methods described herein facilitate relatively straightforward implantation of an ICM into a patient. Specifically, the systems and methods described herein facilitate keeping an incision propped open, maneuvering an injector housing within tissue, guiding placement of the ICM, deploying the ICM such that there is little to no space between the ICM and the surrounding tissue, and removing the injector housing after deployment of the ICM is complete.

Although certain embodiments of this disclosure have been described above with a certain degree of particularity, those skilled in the art could make numerous alterations to the disclosed embodiments without departing from the spirit or scope of this disclosure. All directional references (e.g., upper, lower, upward, downward, left, right, leftward, rightward, top, bottom, above, below, vertical, horizontal, clockwise, and counterclockwise) are only used for identification purposes to aid the reader's understanding of the present disclosure, and do not create limitations, particularly as to the position, orientation, or use of the disclosure. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other. It is intended that all matter contained in the above description or shown in the accompanying drawings shall be interpreted as illustrative only and not limiting. Changes in detail or structure may be made without departing from the spirit of the disclosure as defined in the appended claims.

When introducing elements of the present disclosure or the preferred embodiment(s) thereof, the articles "a", "an", "the", and "said" are intended to mean that there are one or more of the elements. The terms "comprising", "including", and "having" are intended to be inclusive and mean that there may be additional elements other than the listed elements.

As various changes could be made in the above constructions without departing from the scope of the disclosure, it is intended that all matter contained in the above description or shown in the accompanying drawings shall be interpreted as illustrative and not in a limiting sense.

What is claimed is:

1. An injection system comprising:
an implantable cardiac monitor (ICM);
an obturator comprising:
a tip;
a handle; and
a shaft extending between the tip and the handle; and
an injector housing comprising:
a tube extending from a first end of the injector housing to a second end of the injector housing, the tube configured to receive the obturator; and
a receptacle in communication with the tube and an external environment, the receptacle configured to receive the ICM.

2. The injection system of claim 1, wherein the tube comprises:
a first tube portion having a first inner diameter; and
a second tube portion having a second inner diameter, wherein the first inner diameter is smaller than the second inner diameter.

3. The injection system of claim 2, wherein the receptacle is in direct communication with the second tube portion.

4. The injection system of claim 1, wherein the receptacle comprises a plurality of protrusions configured to retain the ICM in the receptacle.

5. The injection system of claim 1, wherein the obturator tip is shaped to perform blunt dissection of tissue.

6. The injection system of claim 5, wherein the obturator tip has one of a tapered conical shape, a duckbill shape, an oval shape, a wedge shape, and a hook shape.

7. The injection system of claim 5, wherein the injector housing further comprises an indicator proximate the injector housing first end, the indicator facilitating alignment of the injector housing with an incision made in a patient.

8. A method for operating an injection system, the method comprising:
inserting an obturator into a tube of an injector housing such that the obturator extends from a first end of the injector housing to a second end of the injector housing; and
inserting an implantable cardiac monitor (ICM) into a receptacle of the injector housing, wherein the receptacle is in communication with the tube of the injector housing.

9. The method of claim 8, further comprising:
making an incision in a patient;
inserting at least a portion of the injector housing into the incision;
withdrawing the obturator from the tube in a first direction until the ICM drops into the tube; and
advancing the obturator in a second direction opposite the first direction to discharge the ICM from the tube.

10. The method of claim 9, further comprising aligning an indicator formed proximate the injector housing first end with the incision prior to advancing the obturator.

11. The method of claim 9, further comprising performing blunt dissection on tissue of the patient using a tip of the obturator.

12. The method of claim 8, wherein inserting an obturator comprises inserting the obturator into a tube that includes a first tube portion having a first inner diameter, and a second tube portion having a second inner diameter, wherein the first inner diameter is smaller than the second inner diameter.

13. The method of claim 8, wherein inserting an ICM comprises inserting the ICM into a receptacle that includes a plurality of protrusions configured to retain the ICM in the receptacle.

14. The method of claim 8, wherein inserting an obturator comprises inserting an obturator that includes a tip having one of a tapered conical shape, a duckbill shape, an oval shape, a wedge shape, and a hook shape.

* * * * *